United States Patent [19]

Kanzelberger

[11] 3,940,864

[45] Mar. 2, 1976

[54] PLASTIC PLATES ADAPTED TO BE IMPRINTED AND METHODS OF MANUFACTURING AND IMPRINTING ON PLASTIC PLATES

[75] Inventor: James C. Kanzelberger, Riverside, Ill.

[73] Assignee: Contemporary, Inc., Manitowoc, Wis.

[22] Filed: Mar. 25, 1974

[21] Appl. No.: 454,166

[52] U.S. Cl. ...................... 40/136; 428/40; 428/41; 428/43; 428/44; 428/101; 428/192; 428/161; 428/480; 428/483; 428/343; 428/352; 156/220; 156/257

[51] Int. Cl.[2]. G09F 7/00; A61F 13/02; E04F 13/20

[58] Field of Search ........... 161/116, 117, 118, 122, 161/145, 146, 149, 167, 231, 182, 406, 406 T; 156/230, 235, 241; 101/32; 117/3.1, 3.2, 38; 40/136; 428/43, 41, 42, 46, 99, 101, 192

[56] References Cited

UNITED STATES PATENTS

| | | | |
|---|---|---|---|
| 2,539,303 | 1/1951 | Gerke et al. | 101/32 |
| 3,089,800 | 5/1963 | Colfer et al. | 161/145 |
| 3,265,524 | 8/1966 | Echeagaray | 161/410 UX |
| 3,276,933 | 10/1966 | Brandt | 117/3.1 X |
| 3,366,042 | 1/1968 | Birch | 101/32 X |
| 3,490,362 | 1/1970 | Massari | 101/32 UX |
| 3,503,835 | 3/1970 | Hermann | 161/146 X |
| 3,519,124 | 7/1970 | Barker et al. | 161/149 X |
| 3,546,053 | 12/1970 | Goldberg et al. | 161/146 |
| 3,595,166 | 7/1971 | Sherman | 161/149 X |
| 3,650,794 | 3/1972 | Steinbach | 161/149 X |
| 3,670,434 | 6/1972 | Shibata et al. | 161/146 UX |
| 3,737,364 | 6/1973 | Hein | 161/149 X |
| 3,770,479 | 11/1973 | Dunning | 117/11 X |

OTHER PUBLICATIONS

Advertising Sheet on Vinyl Laminates, Flexcon Company, Inc., Wall St., Spencer, Mass. 01562.

*Primary Examiner*—George F. Lesmes
*Assistant Examiner*—Alan T. McDonald
*Attorney, Agent, or Firm*—Laff, Whitesel & Rockman

[57] ABSTRACT

An article capable of being hot stamped with desired lettering or designs comprising a plastic laminate and an overlying carrier film with colored matter attached to an appendage portion of the plastic laminate. The back of the laminate has a pressure-sensitive adhesive protected by a removable covering or backing. The method of imprinting and using the article comprises hot stamping the foil and underlying plastic laminate to form the desired lettering or design, removing the foil and appendage portion from the plastic laminate, removing the protective backing to expose the adhesive and to affix the imprinted laminate to a plaque or other item. The process of imprinting on the article includes hot stamping the laminate to deboss it and transfer the coloring matter to the debossed portions, and removing the carrier film. The process for forming the article includes cutting the plastic laminate and carrier film to a desired size and shape, slitting the laminate to form a plate portion and an appendage portion, and securing the carrier film to the appendage portion.

7 Claims, 7 Drawing Figures

PLASTIC PLATES ADAPTED TO BE IMPRINTED AND METHODS OF MANUFACTURING AND IMPRINTING ON PLASTIC PLATES

BACKGROUND OF THE INVENTION

This invention relates to an article with a surface capable of being imprinted. In particular, the invention relates to plastic articles, such as plates, suitable for imprinting by a hot-stamping process and to methods for manufacturing and using these articles.

Decorative plates are used to personalize many items. For example, trophies and plaques given as recognition of an achievement usually hone a plate which contains the recipient's name and other pertinent information. Other uses for such plates include personalization of desk sets, luggage, automobiles and works of art.

Heretofore, most aesthetically acceptable plates have been produced on a metallic material, usually gold or silver in color. Generally, these plates have been imprinted by an engraving method. The method is performed by etching the metallic plate, such as brass or aluminum, with a diamond or carbide stylus. To achieve proper form and arrangement of lettering or other engraved material, a pantograph is generally used.

"Lettering" as used herein means any reproduction of a letter, numeral, design, logotype, trademark or the like.

Although the imprinted plates made by the engraving method have high aesthetic qualities, they often have a disadvantage resulting from the lack of contrast between the imprinted lettering and the remaining surface of the plate. As a result, it may be difficult to read the imprinted lettering. In metal plates, an oxidation process may be employed to obtain contrast, but in most cases the extra cost of this process is prohibitive. Also, contrast has been obtained on plastic plates by using contrasting colors of laminated plastic, but this material and the process of engraving it are expensive.

A second prior art method of imprinting on plates is silk-screening by which coloring matter, such as ink, paint or dye is forced with a squeegie onto the plate through the meshes of a silk or organdy screen so prepared as to have pervious lettered areas and impervious nonlettered areas. Although there may be a high degree of contrast between the lettered and the remaining portion of the plate, a debossed surface cannot be achieved by the silk-screen method. Thus, silk-screening cannot be used where an engraved appearance or effect is desired.

Another disadvantage of the silk-screen method is that it is frequently impractical for personalizing individual plates. This results from the long set up time necessary to prepare the silkscreen for printing. The consequent set-up cost may be acceptable when printing, for example, a few hundred plates, but the additional cost will often be prohibitive when printing only one.

A major problem with the engraving and the silk-screening methods is the requirement that a skilled person perform either method. Thus, neither method is geared for immediate use by the general retail trade. In the case of engraving, the retailer usually sends the item to a jeweler. In the case of silkscreening, the retailer usually sends the item to a printer. The additional time and handling, together with the consequent increased cost, lessen "impulse" purchases which is important in the retail marketing of a relatively low-cost item with an engraved plate.

Another means for imprinting on objects is hot stamping. This technique has been used to imprint such materials as paper, leather, and plastic; but the process does not achieve a high quality engraved-like debossed effect on these materials. Furthermore, hot stamping is not an acceptable technique for imprinting on metal surfaces. Therefore, this technique is not used to imprint metal plates and cannot be used effectively to deboss such metal plates.

Accordingly, an object of the present invention is to provide an improved article with a surface which can be imprinted by a hot-stamping process. Another object is to provide an article with a metallic-like surface which can be imprinted by a hot-stamping method to achieve a high color contrast and a debossed character comparable to an engraved metal plate. Another object of the present invention is to provide a method of imprinting a plate which may be performed by an unskilled operator at the point of sale. Still another object of the invention is to produce a debossed high contrast imprinted plate having superior aesthetic qualities at a low cost. Another object is to provide a plate on which certain common processing mistakes may be inexpensively, easily and quickly corrected. A further object is to provide a plate which may be readily and inexpensively manufactured.

Further objects will become manifest from the description, drawings and claims.

SUMMARY OF THE INVENTION

In one form the invention is an article of a preselected size and shape comprising a plastic laminate with a colored hot-stamping foil superimposed thereon. The foil is adhered to an appendage portion of the plastic laminate. The back of the laminate contains a pressure-sensitive adhesive protected by backing paper. This laminate is adapted to be hot stamped with desired lettering. After the stamping operation, the backing paper is removed to expose the adhesive and separate the imprinted plate from the appendage portion and the foil. The resulting plate has high contrast lettering with excellent aesthetic properties and the plate may be affixed to many types of objects, such as plaques, commemorative keepsakes, trophies, etc.

The process for manufacturing the plate of this invention comprises, in one form, cutting the plastic laminate and the foil to a desired size and shape, slitting the plastic laminate to form a plate portion and appendage portion, applying an adhesive to the appendage, superimposing the foil over the plate and appendage portions and applying pressure to adhere the foil to the appendage portion.

DESCRIPTION OF THE PREFERRED EMBODIMENTS OF THIS INVENTION

Figure 3:
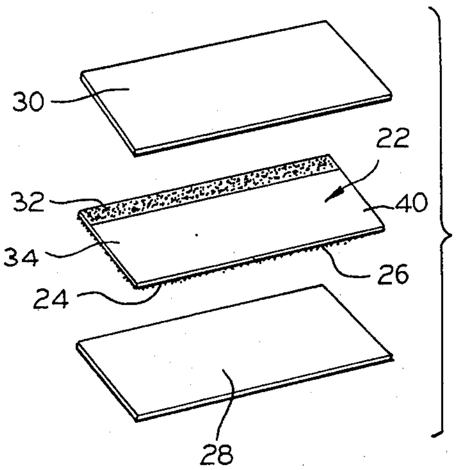
FIG. 3 is an exploded view of the layers of the article of FIG. 1.
Figure 1:
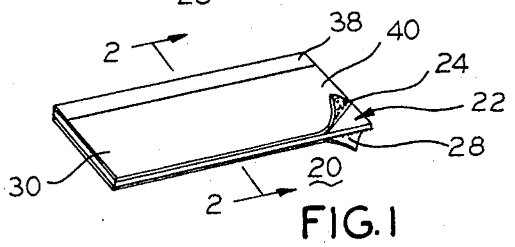
FIG. 1 is a perspective view of one embodiment of the article of this invention.
Figure 2:
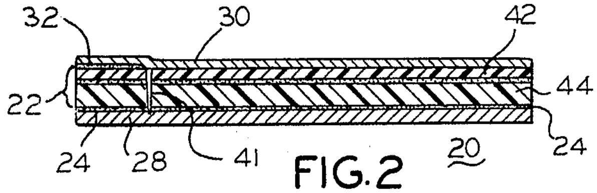
FIG. 2 is a cross-sectional view taken along line 2—2 of FIG. 1.

As illustrated by FIGS. 1–3, the article 20 comprises a plastic laminate or pad 22 of a preselected size and shape having a pressure-sensitive adhesive 24 on the back 26 of laminate 22. The adhesive coating 24 is covered by a backing sheet 28, which is preferably chemically treated, such as by applying a silicone or waxed release surface, in order to prevent strong adhesion to the adhesive coating 24.

A hot-stamping foil 30 is superimposed over the plastic laminate 22. A second adhesive coating 32 is located on an appendage 38 on the front 34 of the plastic laminate 22. This adhesive retains the hot-stamping foil 30 to plastic laminate 22. Other suitable means may be employed for retaining the foil 30 to the plastic laminate, such as stapling. The appendage 38 is removable from the remainder or plate portion 40 by means of a slit 41. Backing sheet 28 maintains appendage portion 38 in contiguous relation with plate portion 40 so that the entire article 20 is self-contained during the hot-stamping operation hereinafter discussed.

Figure 4:
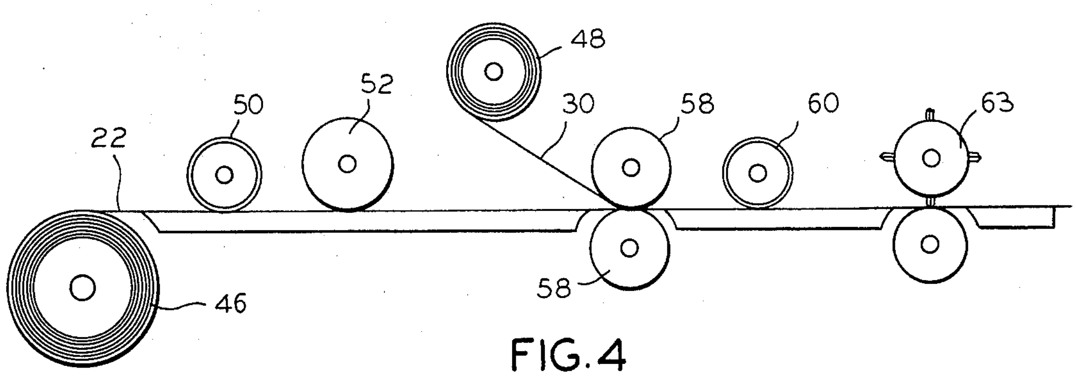
FIGS. 4 and 5 schematically illustrate an exemplary method and apparatus of manufacturing the article of FIG. 1.

The plastic laminate 22 comprises a polyester film 42 laminated on a thermoplastic material 44 (FIG. 4). Applicant has found "metallized" MYLAR to be a satisfactory polyester film (MYLAR is a trademark for polyester film of the du Pont Company). Metallized MYLAR which has the aesthetic properties of gold or silver is readily available from various manufacturers, such as Flexcon Company, Inc.

The thermoplastic material 44 should be readily formable through the application of moderate heat and pressure and a pressure-sensitive adhesive should adhere to it. The film 44 should also be sufficiently rigid to function as a printable plate. Applicant has found rigid polyvinyl chloride to be satisfactory.

In one form, article 20 was constructed using a laminate 22 of MYLAR film having a thickness ranging from ½ to 1 mil and rigid vinyl with a thickness of about 8 mils. Within this range, applicant has found that the plastic laminate 22 was sufficiently rigid and thick to withstand hot stamping and to provide a suitable imprinting surface.

For the adhesive backing 24, a number of compositions, generally known as "pressure-sensitive adhesives," can be used. These are various blends of natural and synthetic rubbers with resins, polyvinyl acetates, ethylene-polyvinyl acetate copolymers (EVA), polyterpenes, hydrogenated resins, resin ester, acrylics, chlorinated paraffins, ethyl cellulose, and a variety of other substances. Common and well-known types of pressure-sensitive adhesives are exemplified by those used on transparent cellophane adhesive tapes. These materials may be applied as solutions using solvents such as naphthas, toluene, chlorinated hydrocarbons, and the like. An important property is that the adhesive be capable of adherence to metal, wood and other types of surfaces used for the products to which the plates of this invention are intended to be attached. The protective cover 28 may be paper, plastic, or other suitable material having desirable releasing properties.

The hot-stamping foil 30 consists of a carrier supporting a coloring matter such as ink. Generally, the carrier is MYLAR, cellophane or acetate. The foil is available in many colors so that various degrees of contrast between the lettering and the remaining plate surface may be achieved. Distributors of suitable hot-stamping foils include Howard Corp., Franklin Corp., and Kingsley Corp.

It should be noted that the rectangular shape of product 20 in this embodiment is merely illustrated as an example. The invention is not limited to any particular shape or size.

Figure 5:
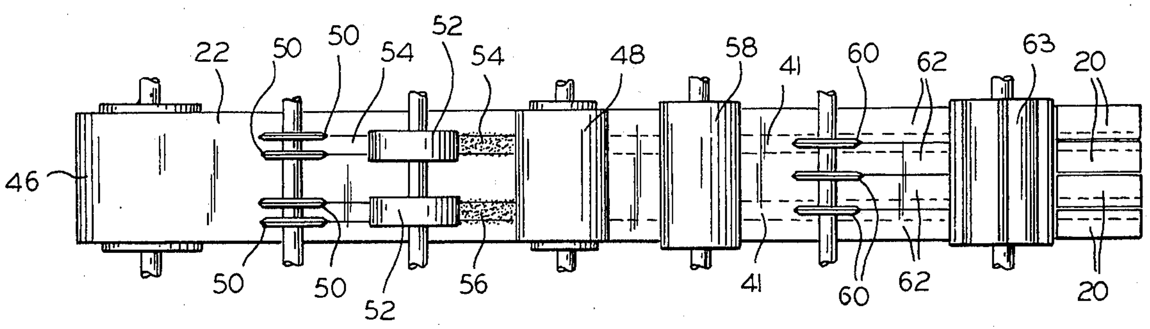
Figure 6:
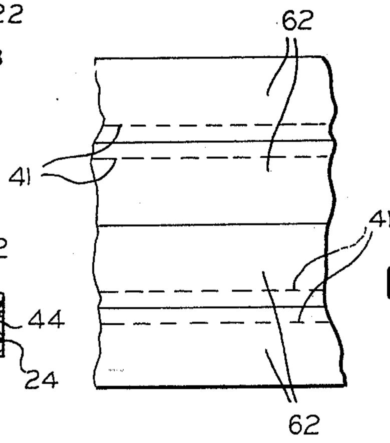
FIG. 6 is a fragmentary view of the article of FIG. 1 as it appears during the process of manufacture illustrated in FIGS. 4–5.

FIGS. 4–6 disclose an exemplary method of manufacture which may be used to produce the article of this invention. The method illustrated may be performed on a Webtron Printing Machine.

In the preferred embodiment, the plastic laminate 22 having adhesive 24 on one side protected by the backing paper 28 is first manufactured in any convenient manner and rolled into a supply roll 46. Likewise, the hot-stamping foil 30 is manufactured in any conventional manner and rolled into supply roll 48.

In one form, the width of the material 22, 30 on each of the supply rolls 46, 48, respectively, is 4½ inches. This material is slit into four ribbons or strips 62 which are 1⅛ inches wide. Each strip 62 consists of plate material 64 which is ⅞ inch wide and appendage material 66 which is ¼ inch wide. The finished product 20 is thus 1⅛ inches wide, and the imprinted plate is ⅞ inch wide.

The plastic laminate web 22 is drawn from supply roll 46 under slitters 50 which cut only through the plastic laminate 22. The backing paper 28 is not cut; it remains intact. Next, adhesive impregnated rollers 52 apply adhesive between the cut or slitted areas 54, 56. The supply roll 48 of hot-stamping foil 30 is drawn into contact with the adhesive-coated laminated material 22. Pressure roll 58 aids in assuring adhesion of hot-stamping foil 30 to the slitted areas 54 and 56 of the plastic laminate 22.

Cutting wheel 60 longitudinally divides the web into the four strips 62. Transverse cutting wheel 63 divides the strips 62 into the completed articles 20. It should be noted that the rectangular article 20 could be die cut into other desired shapes by suitable die cutting apparatus (not shown).

Figure 7:
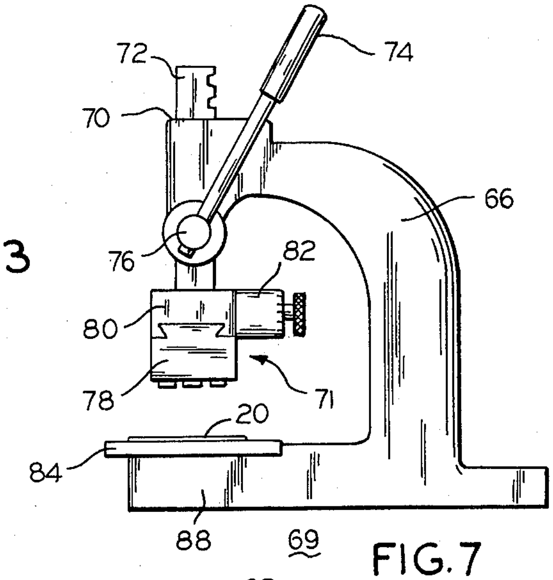
FIG. 7 is a side view of a hot-stamping machine capable of imprinting the article of FIG. 1.

The article 20 may be hot stamped on a conventional hot-stamping machine 69, as illustrated, for example in FIG. 7. The machine 69 comprises support member 66 suitably mounted onto base member 88. The upper portion of the support member 88 has a ram-receiving aperture 70. Stamping means 71 includes a spring-biased ram 72 slidably mounted within ram-receiving aperture 70 and articulated by handle 74 through gear means 76. A heat conductive type stick 78, containing preselected type, is mounted onto a heat conductive mandril portion 80 of ram 72. A heating means 82 supplies thermal energy to the type stick 78.

After the type has been set and the type stick 78 has been inserted into the mandril portion 80, the article 20 is aligned by suitable means on base plate 84. Responsive to the activation of handle 74, stamping means 71 is forced downwardly onto article 20 and heat is concurrently applied, thereby debossing the article 20 while transferring ink from the hot-stamp foil to the debossed letters. The temperature and time at which the stamping operation is carried out are related functions. If the temperature is increased, the time of contact between the stamping means and the object being stamped may be decreased; and the converse is likewise true. It has been found that a hot stamp temperature range of between 150° and 300° will give satisfactory debossing results. At these temperatures, the time range may vary from a fraction of a second to three seconds. At a temperature of 250° F., a stamping time of between one and one and one-half seconds is satisfactory. The hot-stamping foil 30 selected for this process should accommodate the temperatures used and the materials being stamped.

A further function of the stamping operation is the pressure applied to the stamping means. In hand-operated stamping equipment, normal hot-stamping pressures may be satisfactorily applied. One of the advantages of applicant's process is that, where too little or too much pressure has been applied, measures can be taken to correct the plate being imprinted. If the operator exceeds the proper pressure or stamping time, a conventional burnishing stick may be rubbed over the surface of the plate to remove excess ink. If the operator uses too little pressure or time, the plate may be easily corrected by restamping.

Once the article 20 has been hot stamped, the backing sheet 28 is removed and the plate portion 40 is separated from appendage portion 38 and foil 30 (as best illustrated in FIG. 3). The plate portion 40 may then be applied to a plaque or other object.

It is to be understood that the embodiments of the invention which have been described are merely illustrative of the application of the principles of the invention. Numerous modifications may be made by those skilled in the art without departing from the true spirit and scope of the invention, and it is intended that these modifications be included in the claims.

I claim:

1. An article which may be imprinted by a hot-stamping process, comprising a discrete pad of a predetermined augmented plaque size having at least three superimposed layers, a first of said layers being a hot-stamping foil having an overlying coloring matter which transfers from said foil when said foil is subjected to heat and pressure, and a second of said layers comprising a plate of plastic material having a heat deformable characteristic such that said material debosses under said heat and pressure, said plate being separable along an edge in the augmented dimension to form an appendage portion and a separate plaque-sized plate portion, said first layer being attached to said appendage with said coloring matter in face-to-face contact with at least part of said plate portion, said plate having an adhesive on a side opposite the foil, whereby said plate material is debossable and said coloring matter will be deposited in the debossment when said plate is subjected to localized heat and pressure.

2. The article of claim 1 wherein said adhesive is a pressure sensitive adhesive and has a release surface in face-to-face relation with said pressure sensitive adhesive.

3. The article of claim 2 wherein the pressure-sensitive adhesive is protected by a removable backing, which, when removed, separates the plate portion from the appendage portion and the foil.

4. The article of claim 2 wherein said second layer is a thermoplastic material with a polyester film laminated thereto to form a surface for receiving said ink.

5. The article of claim 4 wherein the thermoplastic material is vinyl and the polyester film is MYLAR having a metallic appearance.

6. The article of claim 4 wherein the thermoplastic material is vinyl having a thickness of about 8 mils and the polyester film has a thickness ranging from ½ to 1 mils and has a metallic appearance.

7. The article of claim 1 and indicia formed by hot stamping said pad of layers to deboss an image in said plastic plate portion with said coloring matter embedded in said debossment.

* * * * *